United States Patent
Broemmel et al.

(10) Patent No.: US 10,457,798 B2
(45) Date of Patent: *Oct. 29, 2019

(54) PNEUMATIC TIRE HAVING TREAD WITH HYDROXY-TERMINATED POLYBUTADIENE

(71) Applicant: The Goodyear Tire & Rubber Company, Akron, OH (US)

(72) Inventors: Antonia Felicitas Broemmel, Frankfurt am Main (DE); Julia Martine Francoise Claudine Tahon, Reckange (LU); Timo Benjamin Korfmann, Mainz (DE); Lisa Mailaender, Idstein (DE); Christian Jean-Marie Kaes, Schrondweiler (LU)

(73) Assignee: The Goodyear Tire & Rubber Company, Akron, OH (US)

( * ) Notice: Subject to any disclaimer, the term of this patent is extended or adjusted under 35 U.S.C. 154(b) by 156 days.

This patent is subject to a terminal disclaimer.

(21) Appl. No.: 15/782,134

(22) Filed: Oct. 12, 2017

(65) Prior Publication Data

US 2019/0062534 A1    Feb. 28, 2019

Related U.S. Application Data

(60) Provisional application No. 62/551,976, filed on Aug. 30, 2017.

(51) Int. Cl.
| | |
|---|---|
| *B60C 1/00* | (2006.01) |
| *C08L 9/06* | (2006.01) |
| *C08K 5/5419* | (2006.01) |
| *C08F 236/06* | (2006.01) |
| *C08F 212/08* | (2006.01) |
| *G01N 25/48* | (2006.01) |

(52) U.S. Cl.
CPC ............... *C08L 9/06* (2013.01); *B60C 1/00* (2013.01); *C08F 212/08* (2013.01); *C08F 236/06* (2013.01); *C08K 5/5419* (2013.01); *C08F 2500/02* (2013.01); *G01N 25/4866* (2013.01)

(58) Field of Classification Search
None
See application file for complete search history.

(56) References Cited

U.S. PATENT DOCUMENTS

| | | | |
|---|---|---|---|
| 4,843,120 A | 6/1989 | Halasa | |
| 5,047,483 A | 9/1991 | Halasa | |
| 5,061,765 A | 10/1991 | Hsu | |
| 5,137,998 A | 8/1992 | Hsu | |
| 5,239,009 A | 8/1993 | Halasa | |
| 5,272,220 A | 12/1993 | Rodgers | |
| 5,405,927 A | 4/1995 | Hsu | |
| 5,620,939 A | 4/1997 | Halasa | |
| 5,627,237 A | 5/1997 | Halasa | |
| 5,654,384 A | 8/1997 | Halasa | |
| 5,677,402 A | 10/1997 | Halasa | |
| 6,103,842 A | 8/2000 | Halasa | |
| 6,251,992 B1 * | 6/2001 | Sandstrom | B60C 1/00 152/209.1 |
| 6,559,240 B2 | 5/2003 | Hsu | |
| 7,342,070 B2 | 3/2008 | Tsukimawashi | |
| 8,217,103 B2 | 7/2012 | Thiele | |
| 8,569,409 B2 | 10/2013 | Thiele | |
| 2002/0082333 A1 * | 6/2002 | Herpich | C08G 18/289 524/492 |
| 2011/0301261 A1 * | 12/2011 | Thiele | B60C 1/0016 523/155 |
| 2012/0138203 A1 * | 6/2012 | Kaes | B60C 1/0016 152/450 |
| 2012/0157568 A1 * | 6/2012 | Sandstrom | B60C 1/0016 523/156 |
| 2012/0252952 A1 * | 10/2012 | Thiele | B60C 1/0016 524/425 |
| 2012/0253952 A1 * | 10/2012 | Rafenomanjato | G06Q 30/02 705/14.73 |

FOREIGN PATENT DOCUMENTS

| | | | | |
|---|---|---|---|---|
| DE | 102011055966 A1 | 6/2013 | | |
| EP | 3103655 A1 * | 12/2016 | ........... | B60C 1/0016 |
| EP | 3103655 A1 | 12/2016 | | |
| EP | 3103655 B1 * | 7/2018 | ........... | B60C 1/0016 |
| JP | 2000273240 A | 10/2000 | | |
| JP | 2005126556 A | 5/2005 | | |
| JP | 2006143804 A | 6/2006 | | |
| JP | 4762562 B2 | 6/2011 | | |
| KR | 20140077524 A | 6/2014 | | |
| WO | 2007047943 A2 | 4/2007 | | |

OTHER PUBLICATIONS

European Search Report dated Jan. 9, 2019.

* cited by examiner

*Primary Examiner* — Peter A Salamon

(74) *Attorney, Agent, or Firm* — John D. DeLong

(57) ABSTRACT

The present invention is directed to a pneumatic tire comprising a tread, the tread comprising a rubber composition comprising a diene elastomer, silica, a blocked mercaptosilane, a traction resin, and a low molecular weight polybutadiene functionalized with a hydroxyl functional group.

13 Claims, No Drawings

PNEUMATIC TIRE HAVING TREAD WITH HYDROXY-TERMINATED POLYBUTADIENE

BACKGROUND OF THE INVENTION

It is highly desirable for tires to have good wet skid resistance, low rolling resistance, and good wear characteristics. It has traditionally been very difficult to improve a tire's wear characteristics without sacrificing its wet skid resistance and traction characteristics. These properties depend, to a great extent, on the dynamic viscoelastic properties of the rubbers utilized in making the tire.

In order to reduce the rolling resistance and to improve the treadwear characteristics of tires, rubbers having a high rebound have traditionally been utilized in making tire tread rubber compounds. On the other hand, in order to increase the wet skid resistance of a tire, rubbers which undergo a large energy loss have generally been utilized in the tire's tread. In order to balance these two viscoelastically inconsistent properties, mixtures of various types of synthetic and natural rubber are normally utilized in tire treads. For instance, various mixtures of styrene-butadiene rubber and polybutadiene rubber are commonly used as a rubbery material for automobile tire treads. However, improvements in rolling resistance often occur in tandem with a reduction in wet traction, and vice versa. There is a continuing need, therefore, to develop tread having both good rolling resistance and wet traction.

SUMMARY OF THE INVENTION

The present invention is directed to a pneumatic tire comprising a tread, the tread comprising a rubber composition comprising a diene elastomer, silica, a blocked mercaptosilane, a traction resin, and a low molecular weight polybutadiene functionalized with a hydroxyl functional group.

DETAILED DESCRIPTION OF THE INVENTION

There is disclosed a pneumatic tire comprising a tread, the tread comprising a rubber composition comprising a diene elastomer, silica, a blocked mercaptosilane, a traction resin, and a low molecular weight polybutadiene functionalized with a hydroxyl functional group.

In one embodiment, the rubber composition comprises as the diene elastomer, from 70 to 90 phr of at least one styrene-butadiene rubber, and from 10 to 30 phr of a natural rubber or synthetic polyisoprene.

In one embodiment, the styrene-butadiene rubber comprises a first styrene-butadiene rubber and a second styrene-butadiene rubber.

In one embodiment, at least one of the first and second styrene-butadiene rubber is functionalized with a alkoxysilane group and at least one group selected from sulfur containing functional group and primary amino functional groups.

In one embodiment as diene elastomer for the rubber composition, the diene elastomer includes A) from 40 to 60 phr of a first styrene-butadiene rubber having a Tg ranging from −70° C. to −5° C. and functionalized with a alkoxysilane group and sulfur containing functional group, B) from 20 to 30 phr of a second styrene-butadiene rubber containing from 25 to 45 percent by weight of styrene, a vinyl 1,2 content of 20 to 60 percent by weight based on the rubber weight, a Tg of from −30° C. to −5° C., and C) from 10 to 30 phr of a natural rubber or synthetic polyisoprene. Alternatively, the first styrene-butadiene rubber has a Tg ranging from −40 to −10° C.

In one embodiment, the rubber composition includes from 40 to 60 phr of a first styrene-butadiene rubber functionalized with an alkoxysilane group and a functional group selected from sulfur containing functional groups and amino functional groups. Suitable sulfur containing groups include thiol, thioether, thioester, sulfide, or sulfanyl group. Suitable amino functional groups include primary, secondary, and tertiary amino groups. Additional examples of rubbers which may be used include solution polymerized styrene-butadiene functionalized with groups such as alkoxy including monoalkoxy, dialkoxy, and trialkoxy, silyl, thiols, thioester, thioether, sulfanyl, mercapto, sulfide, and combinations thereof. Such functionalized solution polymerized polymers may be functionalized at the polymer chain ends for example via functional initiators or terminators, or within the polymer chains for example via functional monomers, or a combination of in-chain and end-of-chain functionalization. Specific examples of suitable functional solution polymerized polymers include those described in U.S. Pat. Nos. 8,217,103 and 8,569,409 having alkoxysilyl and sulfide (i.e. thioether) functionality. Such thiol functionality includes thiol or sulfanyl functionality arising from cleavage of sulfur containing groups during compound processing, such as for example from thioesters and thioethers.

In one embodiment, the styrene-butadiene rubber is obtained by copolymerizing styrene and butadiene, and characterized in that the styrene-butadiene rubber has a thiol group and an alkoxysilyl group which are bonded to the polymer chain. In one embodiment, the alkoxysilyl group is an ethoxysilyl group.

The thiol group may be bonded to any of a polymerization initiating terminal, a polymerization terminating terminal, a main chain of the styrene-butadiene rubber and a side chain, as long as it is bonded to the styrene-butadiene rubber chain. However, the thiol group is preferably introduced to the polymerization initiating terminal or the polymerization terminating terminal, in that the disappearance of energy at a polymer terminal is inhibited to improve hysteresis loss characteristics. The thiol group may further exist as a blocked thiol (also known as blocked mercapto group) having a protective functional group attached to the sulfur atom such as in a thioester or thioether, which is then cleaved to expose the thiol sulfur during rubber mixing.

Further, the content of the alkoxysilyl group bonded to the polymer chain of the (co)polymer rubber is preferably from 0.5 to 200 mmol/kg of (styrene-butadiene rubber. The content is more preferably from 1 to 100 mmol/kg of styrene-butadiene rubber, and particularly preferably from 2 to 50 mmol/kg of styrene-butadiene rubber.

The alkoxysilyl group may be bonded to any of the polymerization initiating terminal, the polymerization terminating terminal, the main chain of the (co)polymer and the side chain, as long as it is bonded to the (co)polymer chain. However, the alkoxysilyl group is preferably introduced to the polymerization initiating terminal or the polymerization terminating terminal, in that the disappearance of energy is inhibited from the (co)polymer terminal to be able to improve hysteresis loss characteristics.

The styrene-butadiene rubber can be produced by polymerizing styrene and butadiene in a hydrocarbon solvent by anionic polymerization using an organic alkali metal and/or an organic alkali earth metal as an initiator, adding a terminating agent compound having a primary amino group protected with a protective group and/or a thiol group protected with a protecting group and an alkoxysilyl group to react it with a living polymer chain terminal at the time when the polymerization has substantially completed, and then conducting deblocking, for example, by hydrolysis or other appropriate procedure. In one embodiment, the styrene-butadiene rubber can be produced as disclosed in U.S. Pat. No. 7,342,070. In another embodiment, the styrene-butadiene rubber can be produced as disclosed in WO 2007/047943.

In one embodiment, the solution polymerized styrene-butadiene rubber is as disclosed in WO 2007/047943 and is functionalized with an alkoxysilane group and a blocked thiol, and comprises the reaction product of a living anionic polymer and a silane-sulfide modifier represented by the formula $(R^4O)_xR^4_ySi—R^5—S—SiR^4_3$ wherein Si is silicon; S is sulfur; O is oxygen; x is an integer selected from 1, 2 and 3; y is an integer selected from 0, 1, and 2; x+y=3; $R^4$ is the same or different and is $(C_1-C_{16})$ alkyl; and $R^5$ is aryl, and alkyl aryl, or $(C_1-C_{16})$ alkyl. In one embodiment, $R^5$ is a $(C_1-C_{16})$ alkyl. In one embodiment, each $R^4$ group is the same or different, and each is independently a $C_1-C_5$ alkyl, and $R^5$ is $C_1-C_5$ alkyl.

The solution polymerized styrene-butadiene rubber has a glass transition temperature in a range from −70° C. to −5° C., alternatively from −40 to −10° C. A reference to glass transition temperature, or Tg, of an elastomer or elastomer composition, where referred to herein, represents the glass transition temperature(s) of the respective elastomer or elastomer composition in its uncured state or possibly a cured state in a case of an elastomer composition. A Tg can be suitably determined as a peak midpoint by a differential scanning calorimeter (DSC) at a temperature rate of increase of 10° C. per minute, for example according to ASTM D7426 or equivalent.

Suitable styrene-butadiene rubbers functionalized with an alkoxysilane group and a thiol group are available commercially, such as Sprintan SLR 4602 from Trinseo.

The rubber composition also contains from 20 to 30 phr of a second styrene-butadiene rubber, wherein the second styrene-butadiene rubber is solution-polymerized styrene-butadiene rubber (SSBR) with a bound styrene content of from 25 to 45 percent by weight, a vinyl 1,2 content of from 20 to 60 percent by weight based on the rubber weight, and a Tg of from about −30° C. to about −5° C. As the second styrene-butadiene rubber, suitable solution polymerized styrene-butadiene rubbers may be made, for example, by organo lithium catalyzation in the presence of an organic hydrocarbon solvent. The polymerizations employed in making the rubbery polymers are typically initiated by adding an organolithium initiator to an organic polymerization medium that contains the monomers. Such polymerizations are typically carried out utilizing continuous polymerization techniques. In such continuous polymerizations, monomers and initiator are continuously added to the organic polymerization medium with the rubbery polymer synthesized being continuously withdrawn. Such continuous polymerizations are typically conducted in a multiple reactor system. Suitable polymerization methods are known in the art, for example as disclosed in U.S. Pat. Nos. 4,843,120; 5,137,998; 5,047,483; 5,272,220; 5,239,009; 5,061,765; 5,405,927; 5,654,384; 5,620,939; 5,627,237; 5,677,402; 6,103,842; and 6,559,240.

As the second styrene-butadiene rubber, suitable solution polymerized styrene-butadiene rubbers are available commercially, such as Tufdene E680 SSBR from Asahi Chemical, F3438 from LG Chem, and the like. Such solution polymerized styrene-butadiene rubber may be tin- or silicon-coupled, as is known in the art. In one embodiment, suitable SSBR may be at least partially silicon-coupled.

The rubber composition also contains from 10 to 30 phr of a natural rubber or synthetic polyisoprene. Such synthetic cis 1,4-polyisoprene and cis 1,4-polyisoprene natural rubber are well known to those having skill in the rubber art.

The term "phr" as used herein, and according to conventional practice, refers to "parts by weight of a respective material per 100 parts by weight of rubber, or elastomer."

The rubber composition also contains from 3 to 10 phr of a blocked mercaptosilane include blocked forms of mercapto alkylalkoxysilanes, such as mercaptopropyl triethoxysilane, mercaptopropyl trimethoxysilane, mercaptopropyl methyldimethoxysilane, mercaptopropyl methyldiethoxy silane, mercaptopropyl dimethymethoxysilane, mercaptoethyl triethoxysilane, and mercaptopropyl tripropoxysilane. In each case a blocking group may be bonded to the mercapto sulfur, such blocking group form thioesters —C(=O)—$C_nH_{2n+1}$, where n is from 1 to 10, thioethers, or silylsulfide groups. In one embodiment, the blocking group is a octanoyl group forming a thioester, and the blocked mercaptosilane is S-octanoylmercaptopropyltriethoxysilane (otherwise known as 3-octanoylthio-1-propyltriethoxysilane) available at NXT from Momentive.

The rubber composition includes a functionalized liquid polymer.

Suitable liquid polymer should have double bonds that can react with sulfur and the polymer matrix to form cross-links. Suitable liquid polymers are derived from conjugated diolefin (or diene) monomers. Such liquid polymers can also contain repeat units which are derived from other monomers which are copolymerizable with conjugated diolefin monomers. For instance, the liquid polymer can also contain repeat units which are derived from vinyl aromatic monomers, such as styrene. Polybutadiene rubber, polyisoprene rubber, styrene-butadiene rubber, isoprene-butadiene rubber, styrene-isoprene rubber and styrene-isoprene-butadiene rubber are some representative examples of polymers which can be used as the liquid polymer.

The liquid polymers are functionalized with at least one functional group including alkoxysilyl, hydroxyl, epoxy groups, amino, carboxyl, maleic groups, and maleimide groups. The liquid polymers may be functionalized at the polymer chain ends for example via functional initiators or terminators, or within the polymer chains for example via functional monomers, or a combination of in-chain and end-of-chain functionalization.

The liquid polymers are low molecular weight rubbery polymers of conjugated diolefin monomers. These low molecular weight rubbery polymers will also typically be comprised of repeat units which are derived from one or more conjugated diolefin monomers. Such low molecular weight rubbers can also, of course, contain repeat units which are derived from other monomers which are copolymerizable with conjugated diolefin monomers. For instance, the low molecular weight rubbery polymer can contain repeat units which are derived from vinyl aromatic monomers, such as styrene. Low molecular weight polybutadiene rubber, low molecular weight polyisoprene rubber, low molecular weight styrene-butadiene rubber, low molecular weight isoprene-butadiene rubber, low molecular weight styrene-isoprene rubber and low molecular weight styrene-isoprene-butadiene rubber are some representative examples of low molecular weight rubbery polymers which can be modified to make the wetting agents of this invention. The low molecular weight rubbery polymer will typically have a weight average molecular weight which is within the range of about 1000 to about 25,000 g/gmol. The low molecular weight rubbery polymer will more typically have a weight average molecular weight which is within the range of about 2000 to about 15,000 g/gmol.

The weight average molecular weight Mw may be measured with gel permeation chromatography (GPC) using polystyrene calibration standards, such as is done according to ASTM 3536. GPC is a well-known method wherein polymers are separated according to molecular size, the largest molecule eluting first. The chromatograph is calibrated using commercially available polystyrene molecular weight standards. The detector used is preferably an ultraviolet detector. The fraction of chains existing as mono chains is determined as the ratio of the areas under the GPC curve, i.e., (mono chain peak area)/(total area).

In one embodiment, the rubber compositions include from 3 to 30 phr, alternatively, 3 to 10 phr of functionalized liquid polymer.

In one embodiment, the rubber composition includes from 3 to 30 phr of a polybutadiene functionalized with primary hydroxyl groups at each terminus and having a molecular weight Mw ranging from 1000 to 25000 g/gmol, alternatively 2000 to 4000 g/gmol, and a Tg ranging from −50° C. to −20° C. In one embodiment, the hydroxyl functionalized polybutadiene is Krasol LBH-P 2000 from Cray Valley.

The rubber composition includes a resin.

In one embodiment, the rubber composition includes from 3 to 10 phr of a resin selected from the group consisting of hydrocarbon resins, phenol/acetylene resins, rosin derived resins and mixtures thereof.

Representative hydrocarbon resins include coumarone-indene-resins, petroleum resins, terpene polymers and mixtures thereof.

Coumarone-indene resins are commercially available in many forms with melting points ranging from 10 to 160° C. (as measured by the ball-and-ring method). Preferably, the melting point ranges from 30 to 100° C. Coumarone-indene resins are well known. Various analysis indicate that such resins are largely polyindene; however, typically contain random polymeric units derived from methyl indene, coumarone, methyl coumarone, styrene and α-methyl styrene.

Petroleum resins are commercially available with softening points ranging from 10° C. to 120° C. Preferably, the softening point ranges from 30 to 100° C. Suitable petroleum resins include both aromatic and nonaromatic types. Several types of petroleum resins are available. Some resins have a low degree of unsaturation and high aromatic content, whereas some are highly unsaturated and yet some contain no aromatic structure at all. Differences in the resins are largely due to the olefins in the feedstock from which the resins are derived. Conventional derivatives in such resins include dicyclopentadiene, cyclopentadiene, their dimers and diolefins such as isoprene and piperylene. Copolymer resins of styrene and α-methyl styrene may also be used.

Terpene polymers are commercially produced from polymerizing a mixture of beta pinene in mineral spirits. The resin is usually supplied in a variety of melting points ranging from 10° C. to 135° C.

Phenol/acetylene resins may be used. Phenol/acetylene resins may be derived by the addition of acetylene to butyl phenol in the presence of zinc naphthlate. Additional examples are derived from alkylphenol and acetylene.

Resins derived from rosin and derivatives may be used in the present invention. Gum and wood rosin have much the same composition, although the amount of the various isomers may vary. They typically contain about 10 percent by weight neutral materials, 53 percent by weight resin acids containing two double bonds, 13 percent by weight of resin acids containing one double bond, 16 percent by weight of completely saturated resin acids and 2 percent of dehydroabietic acid which contains an aromatic ring but no unsaturation. There are also present about 6 percent of oxidized acids. Representative of the diunsaturated acids include abietic acid, levopimaric acid and neoabietic acid. Representative of the monounsaturated acids include dextroplmaris acid and dihydroabietic acid. A representative saturated rosin acid is tetrahydroabietic acid.

In one embodiment, the rubber composition includes from 3 to 10 phr of a polyterpene resin. Suitable polyterpene resins include Sylvares TRB 115 from Arizona Chemical.

The rubber composition may also include from 10 to 25 phr of processing oil. Processing oil may be included in the rubber composition as extending oil typically used to extend elastomers. Processing oil may also be included in the rubber composition by addition of the oil directly during rubber compounding. The processing oil used may include both extending oil present in the elastomers, and process oil added during compounding. Suitable process oils include various oils as are known in the art, including aromatic, paraffinic, naphthenic, vegetable oils, and low PCA oils, such as MES, TDAE, SRAE and heavy naphthenic oils. Suitable low PCA oils include those having a polycyclic aromatic content of less than 3 percent by weight as determined by the IP346 method. Procedures for the IP346 method may be found in *Standard Methods for Analysis & Testing of Petroleum and Related Products* and *British Standard* 2000 *Parts,* 2003, 62nd edition, published by the Institute of Petroleum, United Kingdom.

In the rubber composition, the sum of the amounts of the traction resin, the low molecular weight polybutadiene, and the processing oil ranges from 10 to 45 phr.

The rubber composition includes from about 50 to about 100 phr of silica. In another embodiment, from 50 to 80 phr of silica may be used.

The commonly employed siliceous pigments which may be used in the rubber compound include conventional pyrogenic and precipitated siliceous pigments (silica). In one embodiment, precipitated silica is used. The conventional siliceous pigments employed in this invention are precipitated silicas such as, for example, those obtained by the acidification of a soluble silicate, e.g., sodium silicate.

Such conventional silicas might be characterized, for example, by having a BET surface area, as measured using nitrogen gas. In one embodiment, the BET surface area may be in the range of about 40 to about 600 square meters per gram. In another embodiment, the BET surface area may be in a range of about 80 to about 300 square meters per gram. The BET method of measuring surface area is described in the *Journal of the American Chemical Society*, Volume 60, Page 304 (1930).

The conventional silica may also be characterized by having a dibutylphthalate (DBP) absorption value in a range of about 100 to about 400, alternatively about 150 to about 300.

The conventional silica might be expected to have an average ultimate particle size, for example, in the range of 0.01 to 0.05 micron as determined by the electron microscope, although the silica particles may be even smaller, or possibly larger, in size.

Various commercially available silicas may be used, such as, only for example herein, and without limitation, silicas commercially available from PPG Industries under the Hi-Sil trademark with designations 210, 243, etc; silicas available from Solvay, with, for example, designations of Z1165MP, Z165GR and Zeosil Premium 200MP and silicas available from Degussa AG with, for example, designations VN2 and VN3, etc.

Commonly employed carbon blacks can be used as a conventional filler in an amount ranging from 1 to 10 phr. Representative examples of such carbon blacks include N110, N121, N134, N220, N231, N234, N242, N293, N299, N315, N326, N330, N332, N339, N343, N347, N351, N358, N375, N539, N550, N582, N630, N642, N650, N683, N754, N762, N765, N774, N787, N907, N908, N990 and N991. These carbon blacks have iodine absorptions ranging from 9 to 145 g/kg and DBP number ranging from 34 to 150 $cm^3/100$ g.

In one embodiment, the rubber composition may optionally contain a conventional sulfur containing organosilicon compound. In one embodiment, the sulfur containing organosilicon compounds are the 3,3'-bis(trimethoxy or triethoxy silylpropyl) polysulfides. In one embodiment, the sulfur containing organosilicon compounds are 3,3'-bis(triethoxysilylpropyl) disulfide and/or 3,3'-bis(triethoxysilylpropyl) tetrasulfide.

The amount of the optional sulfur containing organosilicon compound in a rubber composition will vary depending on the level of other additives that are used. Generally speaking, the amount of the compound will range from 0.5 to 20 phr. In one embodiment, the amount will range from 1 to 10 phr.

It is readily understood by those having skill in the art that the rubber composition would be compounded by methods generally known in the rubber compounding art, such as mixing the various sulfur-vulcanizable constituent rubbers with various commonly used additive materials such as, for example, sulfur donors, curing aids, such as activators and retarder, fillers, pigments, fatty acid, zinc oxide, waxes, antioxidants and antiozonants and peptizing agents. As known to those skilled in the art, depending on the intended use of the sulfur vulcanizable and sulfur-vulcanized material (rubbers), the additives mentioned above are selected and commonly used in conventional amounts. Representative examples of sulfur donors include elemental sulfur (free sulfur), an amine disulfide, polymeric polysulfide and sulfur olefin adducts. In one embodiment, the sulfur-vulcanizing agent is elemental sulfur. The sulfur-vulcanizing agent may be used in an amount ranging from 0.5 to 8 phr, alternatively with a range of from 1.5 to 6 phr. Typical amounts of processing aids comprise about 1 to about 50 phr. Typical amounts of antioxidants comprise about 1 to about 5 phr. Representative antioxidants may be, for example, diphenyl-p-phenylenediamine and others, such as, for example, those disclosed in *The Vanderbilt Rubber Handbook* (1978), Pages 344 through 346. Typical amounts of antiozonants comprise about 1 to 5 phr. Typical amounts of fatty acids, if used, which can include stearic acid comprise about 0.5 to about 3 phr. Typical amounts of zinc oxide comprise about 2 to about 5 phr. Typical amounts of waxes comprise about 1 to about 5 phr. Often microcrystalline waxes are used. Typical amounts of peptizers comprise about 0.1 to about 1 phr. Typical peptizers may be, for example, pentachlorothiophenol and dibenzamidodiphenyl disulfide.

Accelerators are used to control the time and/or temperature required for vulcanization and to improve the properties of the vulcanizate. In one embodiment, a single accelerator system may be used, i.e., primary accelerator. The primary accelerator(s) may be used in total amounts ranging from about 0.5 to about 4, alternatively about 0.8 to about 1.5, phr. In another embodiment, combinations of a primary and a secondary accelerator might be used with the secondary accelerator being used in smaller amounts, such as from about 0.05 to about 3 phr, in order to activate and to improve the properties of the vulcanizate. Combinations of these accelerators might be expected to produce a synergistic effect on the final properties and are somewhat better than those produced by use of either accelerator alone. In addition, delayed action accelerators may be used which are not affected by normal processing temperatures but produce a satisfactory cure at ordinary vulcanization temperatures. Vulcanization retarders might also be used. Suitable types of accelerators that may be used in the present invention are amines, disulfides, guanidines, thioureas, thiazoles, thiurams, sulfenamides, dithiocarbamates and xanthates. In one embodiment, the primary accelerator is a sulfenamide. If a second accelerator is used, the secondary accelerator may be a guanidine, dithiocarbamate or thiuram compound.

In one embodiment, the rubber compositions may include from 1 to 10 phr as a vulcanization modifier an α, ω-bis(N,N'-dihydrocarbylthiocarbamamoyldithio)alkane. Suitable α, ω-bis(N,N'-dihydrocarbylthiocarbamamoyldithio)alkanes include 1,2-bis(N,N'-dibenzylthiocarbamoyl-dithio)ethane; 1,3-bis(N,N'-dibenzylthiocarbamoyldithio)propane; 1,4-bis(N,N'-dibenzylthiocarbamoyldithio)butane; 1,5-bis(N,N'-dibenzylthiocarbamoyldithio)pentane; 1,6-bis(N,N'-dibenzylthiocarbamoyldithio)hexane; 1,7-bis(N,N'-dibenzylthiocarbamoyldithio)heptane; 1,8-bis(N,N'-dibenzylthiocarbamoyldithio)octane; 1,9-bis(N,N'-dibenzylthiocarbamoyldithio)nonane; and 1,10-bis(N,N'-dibenzylthiocarbamoyldithio)decane. In one embodiment, the vulcanization modifier is 1,6-bis(N,N'-dibenzylthiocarbamoyldithio)hexane available as Vulcuren from Bayer.

The mixing of the rubber composition can be accomplished by methods known to those having skill in the rubber mixing art. For example, the ingredients are typically mixed in at least two stages, namely, at least one non-productive stage followed by a productive mix stage. The final curatives including sulfur-vulcanizing agents are typically mixed in the final stage which is conventionally called the "productive" mix stage in which the mixing typically occurs at a temperature, or ultimate temperature, lower than the mix temperature(s) than the preceding non-productive mix stage(s). The terms "non-productive" and "productive" mix stages are well known to those having skill in the rubber mixing art. The rubber composition may be subjected to a thermomechanical mixing step. The thermomechanical mixing step generally comprises a mechanical working in a mixer or extruder for a period of time suitable in order to produce a rubber temperature between 140° C. and 190° C. The appropriate duration of the thermomechanical working varies as a function of the operating conditions, and the volume and nature of the components. For example, the thermomechanical working may be from 1 to 20 minutes.

The rubber composition may be incorporated in a variety of rubber components of the tire. For example, the rubber component may be a tread (including tread cap and tread base), sidewall, apex, chafer, sidewall insert, wirecoat or innerliner. In one embodiment, the component is a tread.

The pneumatic tire of the present invention may be a race tire, passenger tire, aircraft tire, agricultural, earthmover, off-the-road, truck tire, and the like. In one embodiment, the tire is a passenger or truck tire. The tire may also be a radial or bias.

Vulcanization of the pneumatic tire of the present invention is generally carried out at conventional temperatures ranging from about 80° C. to 200° C. In one embodiment, the vulcanization is conducted at temperatures ranging from about 110° C. to 180° C. Any of the usual vulcanization processes may be used such as heating in a press or mold, heating with superheated steam or hot air. Such tires can be built, shaped, molded and cured by various methods which are known and will be readily apparent to those having skill in such art.

This invention is illustrated by the following examples that are merely for the purpose of illustration and are not to be regarded as limiting the scope of the invention or the manner in which it can be practiced. Unless specifically indicated otherwise, parts and percentages are given by weight.

EXAMPLE 1

In this example, the effect of a hydroxy-terminated polybutadiene on the performance of a tread compound is illustrated. Rubber compositions were mixed in a multi-step mixing procedure following the recipes in Table 1, with all amounts given in phr. Standard amounts of curatives were also included. Rubber compounds were then cured and tested for rolling resistance (RR) and wet braking performance, with results given in Table 2.

TABLE 1

|  | Sample No. | | |
| --- | --- | --- | --- |
|  | Reference | Example 1 | Example 2 |
| SBR [1] | 49 | 52 | 52 |
| SBR [2] | 30 | 27 | 0 |
| SBR [3] | 0 | 0 | 33.75 |
| Natural Rubber | 21 | 21 | 21 |
| Silica [4] | 70 | 74 | 74 |
| Carbon Black | 3 | 5 | 0 |
| Silane [5] | 5.6 | 0 | 0 |
| Silane [6] | 0 | 5.92 | 5.92 |
| Silane [7] | 0 | 0 | 2 |
| Traction resin [8] | 0 | 4 | 4 |
| Liquid Polymer [9] | 0 | 7 | 7 |
| TDAE oil [10] | 11.25 | 10.125 | 0 |
| Sunflower oil | 5 | 6.3 | 5.3 |

[1] Solution polymerized SBR with styrene content of 21% and 1,2-vinyl content of 50%, Tg = −23° C. obtained from Trinseo as SLR4602.
[2] Solution polymerized SBR with styrene content of 34% and 1,2-vinyl content of 38%, Tg = −28° C. extended with 37.5 phr TDAE oil, obtained as Tufdene E680 from JSR.
[3] Solution polymerized SBR with styrene content of 34% and 1,2-vinyl content of 38%, Tg = −22° C. obtained from LG Chem as F3438.
[4] Zeosil Premium 200MP from Solvay
[5] TESPD type silane coupling agent, as Si266 from Evonik.
[6] S-octanoylmercaptopropyltriethoxysilane, as NXT* from Momentive
[7] TESPD type silane coupling agent, 50% on carbon black as X50S from Evonik.
[8] Polyterpene resin, Tg = 70° C., obtained as Sylvares TRB 115 from Arizona Chemicals.
[9] Polybutadiene end functionalized with hydroxyl groups, Mw = 2100, Tg = −35° C., as Krasol LBH-P 2000 from Cray Valley
[10] Includes extension oil and added oil

TABLE 2

|  | Reference | Example 1 | Example 2 |
| --- | --- | --- | --- |
| RR | 100 | 103 | 107 |
| Wet braking | 100 | 108 | 107 |

As can be seen in Table 2, the overall compromise of wet braking and rolling resistance is improved with the compounds using hydroxy-terminated polybutadiene.

The invention claimed is:

1. A pneumatic tire comprising a tread, the tread comprising a rubber composition comprising a diene elastomer, silica, a blocked mercaptosilane, a traction resin, and a low molecular weight polybutadiene functionalized with a hydroxy functional group.

2. The pneumatic tire of claim 1, wherein the rubber composition comprises as the diene elastomer, from 70 to 90 phr of at least one styrene-butadiene rubber, and from 10 to 30 phr of a natural rubber or synthetic polyisoprene.

3. The pneumatic tire of claim 2, wherein the styrene-butadiene rubber comprises a first styrene-butadiene rubber and a second styrene-butadiene rubber.

4. The pneumatic tire of claim 3, wherein at least one of the first and second styrene-butadiene rubber is functionalized with an alkoxysilane group and at least one group selected from sulfur containing functional group and primary amino functional groups.

5. The pneumatic tire of claim 1, wherein the rubber composition comprises as the diene elastomer A) from 40 to 60 phr of a first styrene-butadiene rubber having a Tg ranging from −70° C. to −5° C. and functionalized with a alkoxysilane group and sulfur containing functional group, B) from 20 to 30 phr of a second styrene-butadiene rubber containing from 25 to 45 percent by weight of styrene, a vinyl 1,2 content of 20 to 60 percent by weight based on the rubber weight, a Tg of from −30° C. to −5° C., and C) from 10 to 30 phr of a natural rubber or synthetic polyisoprene.

6. The pneumatic tire of claim 1, wherein the rubber composition comprises as the blocked mercaptosilane from 3 to 10 phr of S-octanoylmercaptopropyltriethoxysilane.

7. The pneumatic tire of claim 1, wherein the low molecular weight polybutadiene functionalized with a hydroxyl functional group is present in an amount ranging from 3 to 30 phr and has a molecular weight Mw ranging from 1000 to 25000 g/gmol and a Tg ranging from −50° C. to −20° C.

8. The pneumatic tire of claim 1, wherein the rubber composition further comprises a processing oil, and the sum of the amounts of the traction resin, the low molecular weight polybutadiene, and the processing oil ranges from 10 to 45 phr.

9. The pneumatic tire of claim 1, wherein the rubber composition comprises from 50 to 100 phr of silica.

10. The pneumatic tire of claim 1, wherein the first rubber composition comprises from 1 to 10 phr of carbon black.

11. The pneumatic tire of claim 1, wherein the rubber composition includes as the traction resin from 3 to 10 phr of a resin selected from the group consisting of hydrocarbon resins, phenol/acetylene resins, rosin derived resins and mixtures thereof.

12. The pneumatic tire of claim 1, wherein the rubber composition includes as the traction resin from 3 to 10 phr of a polyterpene resin.

13. A pneumatic tire comprising a tread, the tread comprising a rubber composition comprising
100 phr of elastomers consisting of the following A, B, and C:
A) from 40 to 60 phr of a first styrene-butadiene rubber having a Tg ranging from −40° C. to −10° C. and functionalized with a alkoxysilane group and sulfur containing functional group,
B) from 20 to 30 phr of a second styrene-butadiene rubber containing from 25 to 45 percent by weight of styrene, a vinyl 1,2 content of 20 to 60 percent by weight based on the rubber weight, a Tg of from −30° C. to −5° C., and
C) from 10 to 30 phr of a natural rubber or synthetic polyisoprene;
3 to 10 phr of S-octanoylmercaptopropyltriethoxysilane;
3 to 10 phr of a polyterpene resin;
3 to 30 phr of a low molecular weight polybutadiene functionalized with a hydroxyl functional group and having a molecular weight Mw ranging from 1500 to 2500 g/gmol and a Tg ranging from −50° C. to −20° C.;
from 10 to 25 phr of a processing oil;
50 to 100 phr of silica; and
1 to 10 phr of carbon black;
wherein the sum of the amounts of the polyterpene resin, the processing oil, and the low molecular weight polybutadiene ranges from 10 to 45 phr.

* * * * *